United States Patent
Braun et al.

(10) Patent No.: US 6,420,156 B2
(45) Date of Patent: *Jul. 16, 2002

(54) PURIFIED PROTEOLYTIC ENZYME AND METHOD OF PURIFICATION

(75) Inventors: Marcel Braun, Konolfingen (CH); Fred Neumann, Steffisburg (DE)

(73) Assignee: Nestec S.A., Vevy (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/135,436

(22) Filed: Aug. 17, 1998

(30) Foreign Application Priority Data

Aug. 22, 1997 (EP) .......................... 97202591

(51) Int. Cl.⁷ ................................. C12N 9/76
(52) U.S. Cl. ..................................... 435/213
(58) Field of Search ......................... 435/213

(56) References Cited

U.S. PATENT DOCUMENTS

| 3,886,043 A | 5/1975 | Walker et al. ............... 435/213 |
| 4,136,201 A | 1/1979 | Feldman ..................... 426/36 |

FOREIGN PATENT DOCUMENTS

| NL | 6704373 | * 9/1968 |
| WO | WO 09/13638 | 11/1990 |
| WO | WO-9700316 A1 | * 1/1997 |

OTHER PUBLICATIONS

Hazlett et al., "Proteinase K Decreases *Pseudomonas auruginosa* Adhesion to Wounded Cornea", Exp. Eye Res., 55(4), pp. 579–587, in CAPLUS AN:1993:20366,1992.*
Somkuti, G.A., "Control of Lipase Content in Mucor Rennet Preparations", J. Dairy Sci., 57(8), pp. 898–899, in CAPLUS AN: 1974:118816.*
Tietz et al., "A Specific Method for Serum Lipase Determination" (Mar., 1966) Clin. Chim. Acta, 13(3), pp. 352–358.*
Lee et al., "Recombinant Trypsin Production in High Cell Density Fed–Batch Cultures in *Escherichia coli*" (1993) Biotech. Bioeng., 41(8), 781–790.*
Ausubel F.M.: "Current Protocols in Molecular Biology", 1995, Wiley & Sons, N.Y., USA, p. .A.3F.12.

* cited by examiner

Primary Examiner—Jon P. Weber
(74) Attorney, Agent, or Firm—Winston & Strawn

(57) ABSTRACT

A purified protease preparation of chymotrypsin and porcine trypsin is prepared by adjusting the pH of a protease solution comprising chymotrypsin and porcine trypsin to a value of between 6 and 9, maintaining the solution at this pH and at 20–35° C. for at least 15 minutes to at most 120 minutes, so as to allow the proteolytic activity of the proteases to destroy the lipolytic activity of the lipases and phospholipases in the solution. Subsequently, the pH of the solution is reduced to a value of less than or equal to 3.5. The purified protease preparation allows the manufacture of infant formulae containing lecithin which are stable during storage and do not exhibit significant degradation of the added lecithin.

20 Claims, No Drawings

PURIFIED PROTEOLYTIC ENZYME AND METHOD OF PURIFICATION

FIELD OF THE INVENTION

The invention relates to a purified proteolytic enzyme and to a method of purifying a proteolytic enzyme, in particular trypsin.

BACKGROUND ART

Commercial proteases, in particular commercial trypsin, even after purification by a special treatment, for example by double crystallization, contains residual lipases, in particular phospholipase $A_2$, which is particularly resistant to the heat deactivation to which protease is subjected after its use in a hydrolysis process.

Trypsin is commonly used in the manufacture of protein hydrolysates intended in particular to enter into the composition of infant products. To incorporate the protein portion into a finished product, for example an infant milk, any residual lipolytic enzymatic activity resulting from the protein hydrolysate must be removed. This is necessary in order to avoid the appearance of products of degradation of lecithin which is added to the final formula for technological reasons, for example to enhance the wettability of powders, into lysolecithin, in particular during storage. Such breakdown products may manifest themselves both in liquid products and in powders by the appearance of stability or organoleptic defects, for example spots, poor taste, or by their toxicity leading to side effects, for example of an inflammatory type in breastfeeding infants.

However, it is the case that the complete removal of phospholipases in particular is difficult to achieve. The complete purification of proteases generally requires various precipitation steps, chromatographic separations, heat treatments under well-defined conditions or chemical inactivations. The complete removal of phospholipase $A_2$, which is very heat-resistant, requires a prolonged heat treatment which unfortunately also affects the protease.

The aim of the invention is the preparation of a purified protease whose proteolytic activity is quantitatively and qualitatively preserved, but which is free of lipolytic activity, in particular of phospholipase $A_2$, by a simple and inexpensive method.

A method of preparing purified trypsin, described for example in U.S. Pat. No. 3,886,043, is known in which a buffer solution of crystallized trypsin is chromatographed by passing over a resin consisting of a dextran gel with grafted sulphonic groups, with the aim of separating the various active forms of porcine trypsin.

It is also known to prepare a lipase-free microbial rennet, for example by the method described in U.S. Pat. No. 4,136,201, by culturing Mucor miehei on an appropriate nutrient medium. The processes of these patents do not achieve the aim of the present invention.

SUMMARY OF THE INVENTION

The invention relates to a purified proteolytic enzymatic preparation and methods for producing the same, characterized in that it possesses a residual phospholipase $A_2$ activity of at most 20 mU/g of pure enzyme detectable by high performance chromatography analysis of phospholipids after incubating with an infant formula whose phospholipase $A_2$ activity is not detectable, and in that its protease activity is maintained at not less than 75% of the initial activity of the enzyme.

DETAILED DESCRIPTION OF THE INVENTION

The measurements of the enzymatic activities are detailed in the examples hereinafter. In particular, "nondetectable" is understood to mean a residual phospholipase $A_2$ activity of <6 mU/g of enzyme.

The enzyme may be any protease of plant, microbial or animal origin or of biogenetic origin. It is preferably a protease of animal origin, such as pancreatin, particularly trypsin of porcine origin.

The method according to the invention is characterized in that:

1) the pH of a solution of the protease is adjusted to a value of between 6 and 9 and in that the solution is kept at this pH and at 20–35° C. for at least 15 min and at most 120 min, so as to use the proteolytic activity of the protease to destroy the lipolytic activity of the lipases and of the phospholipases of the reaction medium, and
2) the pH of the solution is reduced to a value of less than or equal to 3.5, it being possible to reverse the order of steps 1) and 2) above.

In a preferred embodiment which makes it possible to also remove traces of residual lipases other than phospholipase $A_2$, the method comprises a final heat treatment step, preferably by ultra high temperature (UHT), as is known in the art and is shown in the examples herein. Traces of heat-sensitive lipases are thus removed.

Preferably, the adjustment of the pH to the alkaline region takes place before the reduction of the pH to the acidic region, since it is thus possible to defer the use of the protease. In the variant where the two steps are reversed, the protease should be used immediately after the treatment.

In a preferred embodiment, there is added to the reaction medium a magnesium salt which is soluble in the latter, preferably at the beginning of the reaction, which makes it possible to stabilize the proteases while promoting the degradation of the phospholipases. Magnesium chloride is preferably added in an amount of 10 to 200 mM/l of the reaction medium, for example 50 to 100 mM/l of reaction medium.

The pure protease concentration in the solution before treatment may be between 0.5 and 6%, and is preferably about 2.5% by weight. The invention also relates to a method of preparing an infant formula based on protein hydrolysate, characterized in that a whey product is enzymatically hydrolysed by means of a purified protease above, in that the hydrolysate is treated at 75–85° C./3–5 min, in that liquid fat and minerals are added thereto, in that a UHT treatment is carried out at 125–135° C./2–3 min, then in that carbohydrates, vitamins and trace elements are added thereto, in that the liquid product is sterilized by UHT and in that it is aseptically packaged.

According to a variant of this method, the liquid is dried, in particular spray-dried, after UHT sterilization treatment.

The purified enzyme according to the invention may be used outside the food area in the applications of proteases, for example in the preparation of a nutritional, cosmetic or pharmaceutical composition.

There may be mentioned, in this regard, anti-inflammatory applications, the treatment of digestive disorders, the treatment of thromboses, the treatment of injuries and wounds and the elimination of necrosed tissues for example.

EXAMPLES

The examples below illustrate the invention. In these examples, the parts and percentages are by weight, unless otherwise stated.

Example 1

1 kg of commercially available porcine trypsin 6.0 S (Novo, Denmark) is dissolved in 10 kg of demineralized water at 25° C., with stirring, in a vessel, the protease concentration being 9.1% and the initial pH 5. To ensure that undissolved protease is not carried over to the next step, the solution is transferred to a new vessel.

A dilute aqueous NaOH solution at 1 M/l is added to adjust the pH of the solution to 8. The pH is then kept constant for 15 min by addition, as required, of the aqueous NaOH solution above, for example by means of a pH-stat, with stirring, so as to hydrolyse the phospholipases.

After this treatment, the proteases are stabilized, that is to say trypsin and chymotrypsin, by reducing the pH of the reaction medium to 3 by addition of an aqueous HCl solution at 1 M/l. The solution of proteases may be used immediately in a hydrolysis reaction or stored, for example, at −25° C. for a deferred use.

The analyses below show the enzymatic activity of the purified proteolytic enzyme obtained according to the invention compared with that of the original commercially available crystallized enzyme (trypsin PTN 6.0 S, Novo, Denmark) which has not been subjected to the treatment according to the invention.

1. Determination of phospholipases:

1.1 Determination of phospholipase $A_2$ by a radioisotope method.

The method is based on the cleavage of phosphatidylcholine (C14-dioleyl) by phospholipase $A_2$ and the punctual radiometric detection of the labelled fractions after chromatographic separation.

1.2 Determination of the total phospholipases by titrimetry.

The method is not specific to phospholipase $A_2$ and detects all phospholipases. It is based on the titration of fatty acids released from egg yolk phospholipids (Fluka, Buchs, Switzerland) by phospholipases at pH 8 (maintained by a pH-stat) and at a constant temperature of 40° C. with 1.4 mM of sodium deoxycholate and 3 mM $CaCl_2$. 2 g of purified egg yolk phospholipid are used with addition of 250 mg of turkey egg white trypsin inhibitor (Sigma, St. Louis, USA) per 1 g of trypsin.

2. Determination of lipase and esterase:

2.1 The activity of the lipases is determined by titrimetry using olive oil as substrate in an amount of 100 g/l at a constant pH of 8.9 (pH-stat) in the presence of 1.25 g/l of taurocholate and 82.5 g/l of gum arabic.

2.2 The activity of the esterases is determined using the above method (2.1) but taking medium-chain triglycerides (MCT) as substrate.

3. Determination of proteases:

3.1. For trypsin, the method described by Erlanger et al. in Arch. Biochem. Biophys. 95, 271–278 is used.

3.2. For chymotrypsin, the US Pharmacopoeia XXI (1985) method is used. These methods are conventional and are well known by the skilled artisan. To the extent that further details of these processes are required, the entire content of those documents are incorporated herein by reference.

The results of the analyses of activities in the enzyme preparation are indicated in Table 1 below:

TABLE 1

| Enzyme preparation | Phospholipase $A_2$ (U/g), 1.1 | Phospholipases (U/g) | Lipases (U/g) | Esterase (U/g) | Trypsin (g/kg) | Chymotrypsin (USP/mg) |
|---|---|---|---|---|---|---|
| Purified trypsin PTN 6.0 S according to the invention | <0.0022 | 0.79 | 0.21 | 0.22 | 223 | 41 |
| Original trypsin PTN 6.0 S | 87 | 14 | 0.34 | 0.39 | 213 | 42 |

It is observed that the treatment makes it possible to considerably reduce the activity of enzymes other than proteases, in particular to remove that of phospholipase $A_2$, while maintaining intact the proteolytic activity in terms of quality and quantity, in particular the equilibrium between trypsin (93% activity relative to the untreated enzyme) and chymotrypsin (86% activity relative to the untreated enzyme).

Example 2

1 kg of commercially available porcine trypsin 6.0 S (Novo, Denmark) is dissolved in 10 kg of demineralized water at 25° C., with stirring, in a vessel, the protease concentration being 9.1% and the initial pH 5. To ensure that undissolved protease is not carried over to the next step, the solution is transferred to a new vessel.

224 g of magnesium chloride ($MgCl_2.6\ H_2O$) are added, the pH is adjusted to 8.5 over 15 min with a dilute aqueous NaOH solution at 1 M/l. The medium is allowed to react or 120 min at 25° C. without controlling the pH, so as to hydrolyse the phospholipases.

After this treatment, the proteases, that is to say trypsin and chymotrypsin, are stabilized by reducing the pH of the reaction medium to 3 by addition of an aqueous HCl solution at 1 M/l and the solution is allowed to stand for 16 h at 4° C. The purified trypsin solution is then ready for use.

It is observed that the relative activity of the trypsin is 93% of that of the original trypsin and that the relative activity of the chymotrysin is 86% of that of the original chymotrypsin.

Example 3

The purified enzymatic preparation of Example 2 is used to prepare a hypoallergenic infant formula. Whey proteins are hydrolysed and then the hydrolysate is treated at 75–85° C./3–5 min, fat and minerals are added thereto, a UHT treatment is carried out at 125° C./2 min, then maltodextrin and vitamins are added, the liquid product is sterilized by UHT at 148° C./5 s and aseptically packaged.

To test the residual enzymatic activity, 10 ml of purified trypsin solution according to Example 1 are added to 100 ml of the liquid infant formula above whose phospholipase $A_2$ activity is <6 mU/g trypsin. After mixing, the activities of the lipase and esterase are reduced by a heat treatment at 75–80° C./3–5 min on a water bath. After cooling to room temperature, 55 mg of sodium azide are added and the solution is incubated at 40° C./4 d. After incubation, the phospholipid composition is analysed by high-performance liquid chromatography (HPLC) and the phospholipase $A_2$ activity calculated, expressed in mU/100 g of product (mU -PL-$A_2$), from the differences in the concentration of the lysophospholipids according to the formula:

mU PL-$A_2$=(LPC+LPE) at time t2 minus (LPC+LPE) at time t1 in mg/100 g of product 540 (molecular mass of egg lysolecithins)×(t1−t2)

with LPC=lysophosphatidylcholine and LPE=lysophosphatidylethanolamine,
as well as this value expressed in terms of the concentration of pure trypsin g/100 g, that is to say mU PL-$A_2$/g of pure trypsin.

The degradation of trypsin and or chymotrypsin is also evaluated in % relative to the initial activity, as well as the degradation of the phospholipids after 9 months of storage at 20° C. in % of the original phospholipids.

The results are indicated in Table 2 below:

TABLE 2

| Liquid infant formula | PL-$A_2$ (mU/g of pure trypsin), HPLC | Trypsin (% of initial) | Chymotrypsin (% of initial) | Degradation of the phospholipids (% of initial) |
|---|---|---|---|---|
| Hydrolyzed by purified trypsin PTN 6.0 S according to the invention | 16 | 94 | 75 | <1 |
| Hydrolyzed by the original trypsin PTN 6.0 S | 349000 | 100 | 100 | 100 |

Example 4

An infant formula is prepared as in Example 3, except that a phospholipid is added to the liquid mixture before spray-drying it. It observed that the activity of the phospholipases is strongly linked to the degradation of the phospholipids in the product. Large load volumes, an interrupted production, associated with a high phospholipase activity degrades the phospholipids to a certain degree before the product is dried. The products containing the purified trypsin according to the invention show a considerably lower degradation of the added phospholipids, depending on the total quantity of phospholipids added to the formula, <1%, whereas it represents 20 to 90% when the same trypsin is used which has not been subjected to the purification treatment according to the invention.

Furthermore, SDS-PAGE analysis of the residual proteins and analysis of the immunologic ally active antigens by ELISA did not show significant differences using purified trypsin according to the invention compared with production with the unpurified trypsin.

What is claimed is:

1. A treated non-recombinant proteolytic enzymatic preparation comprising chymotrypsin and porcine trypsin having a residual phospholipase $A_2$ activity of at most 20 mU/g of enzyme detectable by conventional high-performance chromatography analysis of phospholipids after incubating with an infant formula whose phospholipase $A_2$ activity is not detectable, and a protease activity which is maintained at not less than 75% of that of an untreated enzyme preparation.

2. The treated proteolytic enzymatic preparation of claim 1, wherein the residual phospholipase $A_2$ activity is less than about 0.003 percent of the phospholipase $A_2$ activity in the untreated enzyme preparation.

3. The treated proteolytic enzymatic preparation of claim 1, wherein the residual phospholipase $A_2$ activity is less than about 2.2 mU/g of pure enzyme detectable by conventional high performance chromatography analysis of phospholipids after incubating with an infant formula whose phospholipase $A_2$ activity is not detectable.

4. The treated proteolytic enzymatic preparation of claim 1, wherein the residual phospholipase activity is at most 6 percent of that of the untreated enzyme preparation.

5. The treated proteolytic enzymatic preparation of claim 1, wherein trypsin activity is at least 93 percent of that of the untreated enzyme preparation.

6. The treated proteolytic enzymatic preparation of claim 1, wherein the ratio of trypsin activity to chymotrypsin activity in the treated proteolytic enzymatic preparation is within about 92 percent of the ratio of activities in the untreated enzyme preparation.

7. The treated proteolytic enzymatic preparation of claim 1, wherein the treated proteolytic enzymatic preparation is in an aqueous base, further comprising between about 10 to about 200 mM of magnesium ions per liter.

8. The treated proteolytic enzymatic preparation of claim 1, wherein the untreated proteolytic enzymatic preparation comprises about 20 percent by weight of trypsin.

9. The treated non-recombinant proteolytic enzyme preparation of claim 1 wherein the treating process comprises the steps of:
providing an untreated enzyme solution comprising a first quantity of chymotrypsin and porcine trypsin and a second quantity of phospholipase $A_2$;
maintaining the pH of the solution at a pH value of between 6 and 9 and the temperature of the solution at a temperature of between 20° C. and 35° C. for a time between about 15 minutes to about 120 minutes so as to use the proteolytic activity of the trypsin to destroy the activity of phospholipase $A_2$ activity; and
maintaining the pH of the solution to a value less than or equal to 3.5;
wherein the treated enzyme solution comprises a quantity of chymotrypsin and porcine trypsin at least equal to 75% of the first quantity of chymotrypsin and porcine trypsin.

10. The treated proteolytic enzyme preparation of claim 9 wherein the treating process further comprises adding a magnesium salt to the solution.

11. The treated proteolytic enzymatic preparation of claim 10 wherein the magnesium salt is added to achieve a concentration of between about 10 mM/l and about 200 mM/l.

12. A treated non-recombinant proteolytic enzymatic preparation of chymotrypsin and porcine trypsin comprising a residual phospholipase activity of at most 6 percent of that of the untreated enzyme, wherein the enzyme is of animal origin, and wherein the protease activity is maintained at not less than 75% of that of the untreated enzyme preparation.

13. The treated proteolytic enzymatic preparation of claim 12, wherein the residual phospholipase activity is at most 0.79 U/g of pure enzyme preparation.

14. The treated proteolytic enzymatic preparation of claim 12, wherein the untreated enzyme comprises phospholipase $A_2$, and wherein the residual phospholipase $A_2$ activity is less than about 2.2 mU/g of pure enzyme detectable by conventional high performance chromatography analysis of phospholipids after incubating with an infant formula whose phospholipase $A_2$ activity is not detectable.

15. The treated proteolytic enzymatic preparation of claim 12, wherein the untreated enzyme comprises phospholipase $A_2$, and wherein the residual phospholipase $A_2$ activity is at most 20 mU/g of pure enzyme detectable by conventional high performance chromatography analysis of phospholipids after incubating with an infant formula whose phospholipase $A_2$ activity is not detectable.

16. The treated proteolytic enzymatic preparation of claim 12, wherein trypsin activity is at least 93 percent of that of the untreated enzyme preparation.

17. The treated proteolytic enzymatic preparation of claim 12, wherein the ratio of trypsin activity to chymotrypsin activity in the treated proteolytic enzymatic preparation within about 92 percent of the ratio of activities in the untreated enzyme preparation.

18. The treated proteolytic enzymatic preparation of claim 12, wherein the untreated proteolytic enzymatic preparation comprises about 20 percent by weight of trypsin.

19. A treated non-recombinant proteolytic enzyme preparation comprising the product of:

providing an untreated enzyme solution comprising a first quantity of chymotrypsin and porcine trypsin and a second quantity of phospholipase $A_2$;

adding a magnesium salt to the solution;

maintaining the pH of the solution at a pH value of between 6 and 9 and the temperature of the solution at a temperature of between 20° C. and 35° C. for a time between about 15 minutes to about 120 minutes so as to use the proteolytic activity of the trypsin to destroy the activity of phospholipase $A_2$ activity; and maintaining the pH of the solution to a value less than or equal to 3.5;

wherein the treated enzyme solution comprises a quantity of chymotrypsin and porcine trypsin at least equal to 75% of the first quantity of chymotrypsin and porcine trypsin and a quantity of phospholipase $A_2$ of at most 20 mU per gram of chymotrypsin and porcine trypsin.

20. The treated proteolytic enzyme preparation of claim 19 wherein the quantity of phospholipase $A_2$ of at most 6 mU per gram of chymotrypsin and porcine trypsin.

* * * * *